United States Patent
Lee et al.

(10) Patent No.: US 9,321,825 B2
(45) Date of Patent: Apr. 26, 2016

(54) N-TERMINAL MODIFIED PEG-TRAIL

(75) Inventors: Kang Choon Lee, Seoul (KR); Su Young Chae, Gwangju (KR); Yu Seok Youn, Seoul (KR); Won Bae Kim, Seoul (KR); Sung Kwon Lee, Seoul (KR)

(73) Assignee: Theraly Pharmaceuticals Inc., Elkridge, MD (US)

( * ) Notice: Subject to any disclaimer, the term of this patent is extended or adjusted under 35 U.S.C. 154(b) by 953 days.

(21) Appl. No.: 12/304,121

(22) PCT Filed: Jun. 12, 2007

(86) PCT No.: PCT/KR2007/002825
§ 371 (c)(1),
(2), (4) Date: Dec. 10, 2008

(87) PCT Pub. No.: WO2007/145457
PCT Pub. Date: Dec. 21, 2007

(65) Prior Publication Data
US 2009/0203599 A1  Aug. 13, 2009

(30) Foreign Application Priority Data

Jun. 12, 2006  (KR) .................. 10 2006 0052702

(51) Int. Cl.
| C07K 14/52 | (2006.01) |
| C07K 14/525 | (2006.01) |
| A61K 38/19 | (2006.01) |
| A61K 47/48 | (2006.01) |
| C07K 14/705 | (2006.01) |

(52) U.S. Cl.
CPC ......... *C07K 14/70575* (2013.01); *A61K 38/191* (2013.01); *A61K 47/48215* (2013.01); *C07K 14/525* (2013.01); *A61K 38/19* (2013.01); *C07K 14/52* (2013.01); *C07K 2319/73* (2013.01)

(58) Field of Classification Search
None
See application file for complete search history.

(56) References Cited

U.S. PATENT DOCUMENTS

2006/0141561 A1* 6/2006 Kelley et al. ................ 435/69.1

FOREIGN PATENT DOCUMENTS

| KR | 1020020010363 | 2/2002 |
| WO | 9831383 | 7/1998 |
| WO | 0069911 | 11/2000 |
| WO | 04001009 | 12/2003 |
| WO | 2004022004 | 3/2004 |
| WO | 2006042848 | 4/2006 |
| WO | 2007145457 | 12/2007 |

OTHER PUBLICATIONS

Kim et al. The secretable form of trimeric TRAIL, a potent inducer of apoptosis. Biochem Biophys Res Comm 321: 930-935, 2004.*
Youn et al. Biological and physicochemical evaluation of the conformatal stability of tumor necrosis factor-related apoptosis-inducing ligand (TRAIL). Biotechnol Lett 29: 713-721, 2007.*
Kinslter et al. Mono-N-terminal poly(ethylene glycol)-protein conjugates. Adv Drug Delivery Rev 54: 477-485, 2002.*
Chae et al. Mol Cancer Ther 9: 1719-1729, 2010.*
Walczak et al. Tumoricidal activity of tumor necrosis factor-related apoptosis-inducing ligand in vivo. Nat Med 5(2): 157-163, 1999.*
Yoshioka et al. Optimal site-specific PEGylation of mutant TNF-alpha improves its antitumor potency. Biochem Biophys Res Comm 315: 808-814, 2004.*
"TNFSF10" entry from genenames.org/data/hgnc_data.php?hgnc_id=11925; 1 page; downloaded Mar. 8, 2011.*
Wu et al. Regression of human mammary adenocarcinoma by systemic administration of a recombinant gene encoding the hFlex-TRAIL fusion protein. Molec Therapy 3(3): 368-374, 2001.*
Yamamoto, et al., Site-specific PEGylation of a lysine-deficient TNF-α with full bioactivity, Nature Biotechnology, 2003, pp. 546-552, vol. 21.
Xiang, et al., Tissue Distribution, Stability, and Pharmacokinetics of APO2 Ligand/Tumor Necrosis Factor-Related Apoptosis-Inducing Ligand in Human Colon Carncinoma COLO205 Tumor-Bearing Nude Mice, Drug Metabolism and Disposition, 2004,pp. 1230-1238, vol. 32(11).
Shibata; et al, Functionalization of Tumor Necrosis Factor-α Using Phase Display Technique and PEGylation Improves Its Antitumor Therapeutic Window, Clinical Cancer Research, 2004, pp. 8293-8300, vol. 10.
Definition of Dimer, thefreedictionary.com, 2 pages, accessed Dec. 8, 2014.
Definition of Trimer, thefreedictionary.com, 2 pages, accessed Dec. 8, 2014.
Mayo Clinic, "Diabetes", www.mayoclinic.org/diseases-conditions/diabetes/in-depth/diabetes-symthoms/art, 2 pages, accessed Dec. 19, 2014.
Byeon, et al., "Human serum albumin-TRAIL conjugate for the treatment of rheumatoid arthritis", Bioconjug Chem., 25(12):2212-21 (2014).
European Search Report for EP 12804683 Mailed Nov. 20, 2014.
International Search Report and Written Opinion for PCT/US2015/020015 mailed Jul. 8, 2015.
Kim, et al., "Ionic complex systems based on hyaluronic acid and PEGylated TNF-related apoptosis-inducing ligand for treatment of rheumatoid arthritis", Biomaterials, 31(34):9057-64 (2010).
Kim, et al., "PEGylated TNF-related apoptosis-inducing ligand (TRAIL) analogues: pharmacokinetics and antitumor effects", Bioconjug Chem., 22(8):1631-7 (2011a).

(Continued)

*Primary Examiner* — Bridget E Bunner
(74) *Attorney, Agent, or Firm* — Pabst Patent Group LLP

(57) ABSTRACT

Disclosed herein are an N-terminal modified PEG-TRAIL conjugate and a preparation method and use thereof. The PEG-TAIL conjugate has pharmaceutical activity identical or similar to that of native TRAIL (TNF-related apoptosis-inducing ligand) with extended in vivo half-life and enhanced stability. Compared to native TRAIL, the PEG-TAIL conjugate exhibits high solubility and solution stability, with highly improved pharmacokinetic profiles. Thus, the PEG-TAIL conjugate may be very useful for preventing and treating proliferative diseases and autoimmune diseases.

19 Claims, 12 Drawing Sheets

(56) References Cited

OTHER PUBLICATIONS

Kim, et al., "Site-specific PEGylated Exendin-4 modified with a high molecular weight trimeric PEG reduces steric hindrance and increases type 2 antidiabetic therapeutic effects", Bioconjug Chem., 23(11):2214-20 (2012).

Lee, et al., "Treatment with PEGylated TNF-related apoptosis-inducing ligand (TRAIL) induces apoptosis of human arthritis (RA) fibroblast-like synoviocytes (FLS) and suppresses arthritis in murine collagen-induced arthritis", Arthritis and Rheumatism; 72nd Annual scientific meeting of the American college of Rheumatology/43rd annual scientific meeting, Wiley San Francisco, CA, 58(9); Suppl S p. s539, Sep. 1, 2008.

Liao, et al., "Trail reduced joint inflammation, osteoclast activation and and loss in experimental arthritis", Allergy, 68(98):67 (2013).

Ma, et al., "TNF inhibitor therapy for rheumatoid arthritis (Review)", Biomed Reports, 1(2):177-84 (2012).

* cited by examiner

N-TERMINAL MODIFIED PEG-TRAIL

TECHNICAL FIELD

The present invention relates to an N-terminal modified polyethylene glycol (PEG)-TRAIL conjugate and a preparation method and use thereof. More particularly, the present invention relates to an N-terminal modified PEG-TRAIL conjugate in which PEG or a PEG derivative binds to the N-terminus of TRAIL, a method of preparing the conjugate, and an agent for preventing and treating proliferative diseases or autoimmune diseases comprising the conjugate as an effective ingredient.

REFERENCE TO SEQUENCE LISTING

The Sequence Listing submitted Mar. 8, 2016, as a text file named "THER_107_ST25.txt," created on Mar. 8, 2016, and having a size of 5,509 bytes is hereby incorporated by reference.

BACKGROUND ART

Tumor necrosis factor (TNF)-related apoptosis-inducing ligand (TRAIL) is a typical member of the TNF family, and is a membrane protein participating in apoptosis. TRAIL is a protein consisting of 281 amino acids (SEQ ID NO:1: MAMMEVQGGPSLGQTCVLIVIFTVLLQS-LCVAVTYVYFTNELKQMQDKYSKSGIACFL KEDDSYWDPNDEESMNSPCWQVKWQL-RQLVRKMILRTSEETISTVQEKQQNISPLVRE RGPQR-VAAHITGTRGRSNTLSSPNSKNEKALGR-KINSWESSRSGHSFLSNLHLRNGELVI HEKGFYYIYSQTYFRFQEEIKENTKND-KQMVQYIYKYTSYPDPILLMKSARNSCWSKDA EYGLYSIYQGGIFELKENDRIFVSVTNE-HLIDMDHEASFFGAFLVG), in which an extracellular domain comprising amino acids from arginine at position 114 to glycine at position 281 (SEQ ID NO:2: RERGPQRVAA-HITGTRGRSNTLSSPNSKNEKALGR-KINSWESSRSGHSFLSNLHLRNGEL VIHEKGFYY-IYSQTYFRFQEEIKENTKNDKQMVQYIYKYTSYPD-PILLMKSARNSCWSK DAEYGLYSIYQGGIFELKEN-DRIFVSVTNEHLIDMDHEASFFGAFLVG) affects apoptosis. Three molecules of TRAIL form a structurally modified trimer. The TRAIL trimer assembles with receptors participating in cell death to induce apoptosis.

A major difference between TRAIL and other members of the TNF superfamily, such as TNF and CD95L, is its ability not to induce cell death at normal tissues. A variety of medical or pharmaceutical applications have been attempted on TNF and CD95L, because these proteins induce cell death. Since TNF and CD95L proteins affect normal cells and also induce the death of cancer cells and over-activated immune cells, they have limited applicability. In contrast, TRAIL induces apoptosis in a wide range of cancer cells and over-activated immune cells with little effect on normal cells. This is due to the differential expression of TRAIL receptors between cell types. Five TRAIL receptors have been identified. Among them, DR4 (TRAIL-R1) and DR5 (TRAIL-R2) are representative cell death-related receptors. When TRAIL binds to DR4 or DR5, an intracellular death domain of the receptor is activated and thus transduces apoptotic signals via various signal transduction pathways, leading to apoptotic cell death. TRAIL can also bind to DcR1, DcR2 and osteoprotegerin (OPG), which do not induce apoptosis. No marked difference has been seen in the expression levels of the cell death-inducing receptors DR4 and DR5 between normal and tumor cells. In contrast, the three other receptors not inducing apoptosis are expressed at high levels in normal cells, but are either expressed at low levels or are not expressed at all in tumor cells. Thus, in normal cells, TRAIL binds mostly to DcR1, DcR2 and OPG, which do not contain a death domain, and thereby do not induce cell death. In contrast, in cancer cells and over-activated immune cells, apoptosis is induced by the binding of TRAIL to DR4 and DR5, which contain a death domain. Such selective apoptosis induction of TRAIL seems to be a particularly attractive feature in medical or pharmaceutical applications.

TRAIL-mediated apoptosis has been observed in various types of cancer cells, including colon carcinoma, glioma, lung carcinoma, prostate carcinoma, brain tumors and multiple myeloma cells. TRAIL has been proven to have very high anticancer activity in animals. The good anticancer efficacy of TRAIL has been obtained through the use of TRAIL alone, as well as in combination with other anticancer agents, such as paclitaxel and doxorubicin, and radiotherapy. Clinical trials are currently being conducted by Genentech and Amgen using TRAIL, which has good anticancer efficacy in solid tumors. In addition to cancer, various approaches using TRAIL have been made in arthritis, an autoimmune disease, for relieving and treating arthropathy by inducing the death of overactivated immune cells. In addition to protein therapy, gene therapy has been attempted through the delivery of the TRAIL gene. Thus, TRAIL may be useful in the treatment of various aforementioned types of cancer, as well as in the treatment of T cell-mediated autoimmune disorders such as experimental autoimmune encephalomyelitis, rheumatoid arthritis and type I diabetes.

However, native TRAIL has some problems to be overcome for application thereof. The major problem is the low trimer formation ratio of native TRAIL. TRAIL monomers do not bind to the aforementioned TRAIL receptors, and thus do not induce apoptosis. In this regard, many studies have been performed with the goal of improving the trimeric structure and trimer formation ratio of TRAIL. In native TRAIL, the zinc ion has been known to play a critical role in trimerization. In addition, the structural analysis of TRAIL has been conducted using a computer, and mutants of TRAIL have been developed based on the analysis results. For the formation of TRAIL trimers, the most useful method appears to be the introduction of a novel amino acid sequence favoring trimeric folding. Such sequences include a leucine zipper motif and an isoleucine zipper motif. Henning Walczak reported the anticancer efficacy of a trimeric TRAIL derivative in which a leucine zipper motif is added to the N terminus of native TRAIL (H. Walczak, et al. Nature Medicine 1999, 5, 157-163). Dai-Wu Seol et al. reported a TRAIL derivative containing a novel isoleucine zipper motif and having good apoptotic activity (M H Kim, et al. BBRC 2004, 321, 930-935).

Another problem in the clinical applications of TRAIL involves cytotoxicity shown in normal cells of some tissues. Most normal cells are resistant to cytotoxicity, resulting from the expression of the various aforementioned TRAIL receptors, but some hepatocytes and keratinocytes are sensitive to TRAIL-mediated cytotoxicity (H. Yagita, et al. Cancer Sci. 2004, 95, 777-783; M. Jo et al. Nature Medicine 2000, 6, 564-567; S. J. Zheng, et al. J. Clin. Invest. 2004, 113, 58-64).

In addition to toxicity toward some normal cells, TRAIL has a short half-life in vivo, which should be overcome for the successful clinical application of TRAIL. TRAIL has different half-lives according to the species of animals used in tests. For example, TRAIL has been reported to have a half-life of several minutes in rodents and about 30 minutes in apes (H.

Xiang, et al. Drug Metabolism and Disposition 2004, 32, 1230-1238). In particular, most TRAIL is rapidly excreted via the kidneys. This short half-life is considered a drawback to the pharmaceutical usefulness of TRAIL, resulting in a need for TRAIL or derivatives thereof having an extended half-life. Other problems to be solved include the low solubility and solution stability of TRAIL.

Meanwhile, polyethylene glycol (PEG) is a polymer having a structure of HO—(—$CH_2CH_2O$—)$_n$—H. Due to its high hydrophilicity, PEG enables an increase in the solubility of drug proteins when linked thereto. In addition, when suitably linked to a protein, PEG increases the molecular weight of the modified protein while maintaining major biological functions, such as enzyme activity and receptor binding, thereby reducing urinary excretion, protecting the protein from cells and antibodies recognizing exogenous antigens, and decreasing protein degradation by proteases. The molecular weight of PEG, capable of being linked to proteins, ranges from about 1,000 to 100,000. PEG having a molecular weight higher than 1,000 is known to have very low toxicity. PEG having a molecular weight between 1,000 and 6,000 is distributed widely throughout the entire body and is metabolized via the kidney. In particular, PEG having a molecular weight of 40,000 is distributed in the blood and organs, including the liver, and is metabolized in the liver.

In general, medically and pharmaceutically useful proteins administered via parenteral routes are disadvantageous in terms of being immunogenic in the body, being poorly water-soluble and being cleared from circulation within a short period of time. Many studies have been performed to overcome such problems. U.S. Pat. No. 4,179,337 mentions that, when used as therapeutics, pegylated proteins and enzymes have effects including reduced immunogenicity, increased solubility and extended in vivo residence time, which all are advantages of PEG. After this patent, a variety of efforts have been made to overcome the drawbacks of bioactive proteins through pegylation. An example is Veronese et al. pegylated ribonuclease and superoxide dismutase (Veronese et al., 1985). U.S. Pat. Nos. 4,766,106 and 4,917,888 describes the conjugation of proteins to a polymer including PEG to increase the water solubility thereof. In addition, U.S. Pat. No. 4,902,502 describes the conjugation of recombinant proteins to PEG or other polymers to reduce immunogenicity and extend circulating in vivo half-life.

However, despite the aforementioned advantages, there are some problems with protein pegylation, as follows. PEG is typically conjugated to a target protein through covalent bonding to one or more free lysine (Lys) residues. At this time, if PEG is bound to a region directly associated with protein activity among surface regions of the protein, the PEG-attached region loses biological functions, leading to decreased protein activity. Also, since the attachment of PEG to lysine residues mostly occurs in a random manner, various kinds of PEG-protein conjugates, corresponding to particular attachment sites, exist as a mixture. From this mixture, a desired conjugate is difficult to purify and isolate.

TRAIL also harbors problems similar to those caused by pegylation described above. Native TRAIL has eleven lysine residues, some of which participate in the interaction between TRAIL and its cognate receptors or are within an active site. Thus, the addition of polyethylene glycol molecules through the reaction with lysine residues may act as a very important inhibitory factor against the bioactivity of TRAIL. In the case of the TNF superfamily, several studies have noted that the bonding between lysine residues and polyethylene glycol molecules inhibits activation (Y. Yamamoto, et al. Nature Biotechnology 2003, 21, 546-552; H. Shibata et al. Clin. Cancer Res. 2004, 10, 8293-8300).

In this regard, the present inventors selectively attached PEG or a PEG derivative to an N-terminus of TRAIL. Such pegylation was found to reduce drug uptake and removal by hepatocytes and the hepatic reticuloendothelial system, leading to a decrease in TRAIL-mediated hepatoxicity, and remarkably increase the solubility and stability of TRAIL. Also, pegylation was found to improve pharmacokinetic profiles of a linked drug with long-term storage in various formulations, thereby reducing drug administration frequencies and allowing sustained duration of effects of the drug. In this way, the present inventors obtained an N-terminal modified PEG-TRAIL conjugate and found a method of preparing the conjugate, thereby leading to the present invention.

DISCLOSURE

Technical Problem

It is therefore an object of the present invention to provide an N-terminal modified PEG-TRAIL conjugate or a pharmaceutically acceptable salt thereof.

It is another object of the present invention to provide a method of preparing the N-terminal modified PEG-TRAIL conjugate.

It is a further object of the present invention to provide the use of the N-terminal modified PEG-TRAIL conjugate.

Technical Solution

In order to accomplish the above objects, the present invention provides an N-terminal modified PEG-TRAIL conjugate or a pharmaceutically acceptable salt thereof, a method of preparing the same, and a preventive or therapeutic agent for proliferative diseases or autoimmune diseases comprising the same as an effective ingredient.

Advantageous Effects

An N-terminal modified PEG-TRAIL conjugate prepared according to the present invention has very high solubility and stability compared to native TRAIL. Also, the pegylated TRAIL has remarkably increased in vivo half-life while retaining biological activity similar to that of native TRAIL. Thus, the pegylated TRAIL may be very useful as a preventive or therapeutic agent for proliferative diseases or autoimmune diseases.

BEST MODE

Figure 1:
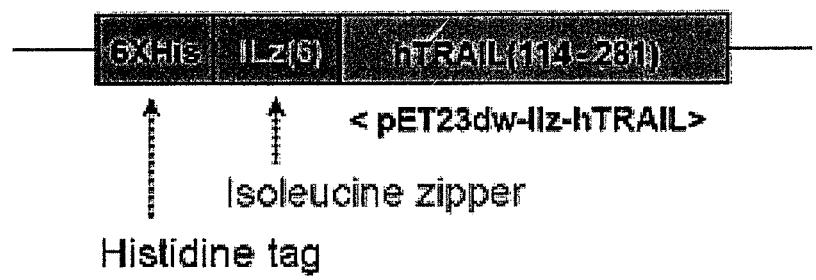
FIG. 1 schematically shows the structure of recombinant hTRAIL (ILz-hTRAIL, monomer) for expressing trimeric hTRAIL.

In one aspect, the present invention provides an N—terminal modified PEG-TRAIL conjugate or a pharmaceutically acceptable salt thereof.

TRAIL may be obtained in a native or genetically engineered (recombinant) form, and may include a zipper amino acid motif favoring trimer formation or a terminal group facilitating isolation and purification thereof.

TRAIL is in the human form, which has an amino acid sequence of 281 amino acids in length, and preferably has an amino acid sequence from arginine-114 to glycine-281 (SEQ ID NO:2) of the full-length human form (1-281, SEQ ID NO:1).

TRAIL may be attached to an isoleucine zipper at its N-terminus.

PEG may include its derivatives.

PEG or its derivatives may be a linear or branched form. Preferably, PEG or its derivatives includes, but is not limited to, methoxy PEG succinimidyl propionate (mPEG-SPA), methoxy PEG N-hydroxysuccinimide (mPEG-NHS), methoxy PEG aldehyde (mPEG-ALD), methoxy PEG maleimide (mPEG-MAL) and multiple-branched PEG.

PEG may have a molecular weight between 1,000 and 40,000, and preferably between 5,000 and 40,000.

In another aspect, the present invention provides a method of preparing the N-terminal modified PEG-TRAIL conjugate.

The N-terminal modified PEG-TRAIL conjugate may be obtained by reacting an N-terminal amine of TRAIL with an aldehyde group of PEG in the presence of a reducing agent.

PEG may include derivatives thereof.

PEG or its derivatives may be in a linear or branched form. Preferably, PEG or its derivatives includes methoxy PEG succinimidyl propionate (mPEG-SPA), methoxy PEG N-hydroxysuccinimide (mPEG-NHS), methoxy PEG aldehyde (mPEG-ALD), methoxy PEG maleimide (mPEG-MAL) and multiple-branched polyethylene glycol derivatives.

PEG may have a molecular weight between 1,000 and 40,000, and preferably between 5,000 and 40,000.

In the present method, PEG and TRAIL react at a molar ratio (PEG/TRAIL) of 2 to 10, and preferably 5 to 7.5.

TRAIL may be obtained in a native or genetically engineered (recombinant) form. Preferably, TRAIL may include a zipper amino acid motif favoring trimer formation or a terminal group facilitating isolation and purification thereof.

TRAIL is in the human form, which has an amino acid sequence of 281 amino acids in length, and preferably has an amino acid sequence from arginine-114 to glycine-281 of the full-length human form (1-281).

TRAIL may be attached to an isoleucine zipper at its N-terminus.

The reducing agent may include $NaCNBH_3$ and $NaBH_4$.

In a further aspect, the present invention provides a preventive or therapeutic agent for a proliferative disease comprising the N-terminal modified PEG-TRAIL conjugate as an effective ingredient.

The proliferative disease is cancer, and preferably includes colon carcinoma, glioma, lung carcinoma, prostate carcinoma, brain tumor and multiple myeloma.

In yet another aspect, the present invention provides a preventive or therapeutic agent for an autoimmune disease comprising the N-terminal modified PEG-TRAIL conjugate as an effective ingredient.

The autoimmune disease includes experimental autoimmune encephalomyelitis, rheumatoid arthritis and type I diabetes.

The preventive or therapeutic agent comprising the N-terminal modified PEG-TRAIL conjugate as an effective ingredient according to the present invention may be formulated into various formulations for oral or parenteral administration upon clinical application, but is not limited thereto.

In the formulation, diluents or excipients may be used, and are exemplified by fillers, thickeners, binders, humectants, disintegrators and surfactants. Examples of solid formulations for oral administration include tablets, pills, powders, granules and capsules. The solid formulations may include, in addition to the PEG-TRAIL conjugate, at least one excipient selected from among starch, calcium carbonate, sucrose, lactose, gelatin, etc. Also, the solid formulations may include, in addition to a simple excipient, a lubricant such as magnesium stearate or talc. Examples of liquid formulations for oral administration include suspensions, internal solutions, emulsions and syrups. The liquid formulations may include, in addition to commonly used simple diluents such as water and liquid paraffin, various excipients, which are exemplified by humectants, sweeteners, aromatics and preservatives. Examples of preparations for parenteral administration include sterile aqueous solutions, non-aqueous solutions, suspensions, emulsions, freeze-dried preparations and suppositories. In the formulation into non-aqueous solutions and suspensions, propylene glycol, PEG, vegetable oils such as olive oil, and injectable esters such as ethyl oleate may be used. A formulation may be supplemented with calcium or vitamin $D_3$ in order to enhance its efficacy as a therapeutic agent for proliferative diseases or autoimmune diseases.

The dosage for a specific patient may vary according to the patient's weight, age, gender, state of health and diet, administration duration, administration routes, excretion rates and severity of illness. Typically, it is possible to administer an effective dosage once every one to two weeks. Also, the dosage may be taken in a single dose or in several divided doses within a daily effective dosage.

MODE FOR INVENTION

A better understanding of the present invention may be obtained through the following examples and test examples, which are set forth to illustrate, but are not to be construed as the limit of the present invention.

Example 1

Preparation of N-Terminal Modified Peg-Trail Conjugate

**1-1: Culture of *E. coli* Transformed with TRAIL Gene and Protein Expression**

The truncated form of human TRAIL (hTRAIL) used in this test contained amino acids spanning from arginine-114 to glycine-281 of the full-length form (1-281) of hTRAIL. The recombinant TRAIL was expressed and produced in *E. coli* BL21 (DE3), and an expression plasmid pET3a was used. An isoleucine zipper (ILz) favoring trimer folding was added to an N-terminus of the recombinant hTRAIL. The recombinant hTRAIL was then tagged with six histidine (6×His) residues at its N-terminal end in order to facilitate isolation and purification. FIG. 1 schematically shows the structure of the resultant recombinant hTRAIL (monomer) for expressing trimeric hTRAIL (His-tagged and isoleucine zipper-linked).

The transformed *E. coli* was cultured in sterile LB medium at 37° C. with agitation for about 12 hrs in the presence of ampicillin (50 mg/L) for selective culture of a transformant. After the transformed *E. coli* was proliferated for the culturing, isopropyl-β-D-thiogalactoside (IPTG) was added to the culture medium to induce the expression of *E. coli* genotype. After the agitating incubator and the *E. coli* culture was reduced to 27° C., 1 ml of 1M IPTG solution was added to the culture medium. The cells were further cultured for about 7 hrs with agitation to induce protein expression. The cultured cells were harvested by centrifugation at 5,000 g for 10 min.

**1-2: Purification of the Recombinant hTRAIL from *E. coli***

The recombinant hTRAIL was isolated from the transformed *E. coli* cells harvested in Example 1-1 using a Ni-affinity chromatography. First, the cell pellet obtained by centrifugation was suspended in 20 mM phosphate buffer (pH 7.5), and sonicated to disrupt the cell membrane, thereby releasing TRAIL expressed in *E. coli*. After insoluble cellular substrates were removed through centrifugation at 10,000 rpm for 20 min, the supernatant was slowly passed through a column pre-packed with Ni-NTA resin. The recombinant hTRAIL was selectively bound to the column through the interaction between the six N-terminally tagged histidine residues and chelating nickel ions. The column was washed with phosphate buffer (pH 7.5) and phosphate buffer containing 10 mM and 50 mM imidazole to eliminate impurities, including proteins other than the recombinant hTRAIL. Then, the recombinant hTRAIL bound to the column was eluted with phosphate buffer containing 500 mM imidazole. The TRAIL-containing elution fractions were subjected to ultrafiltration to remove the high concentrations of imidazole. The finally isolated, purified product was placed in 50 mM acetate buffer at a pH of 5.0 with a high purity (98% or higher). The results are given in FIG. 2.

Figure 2:
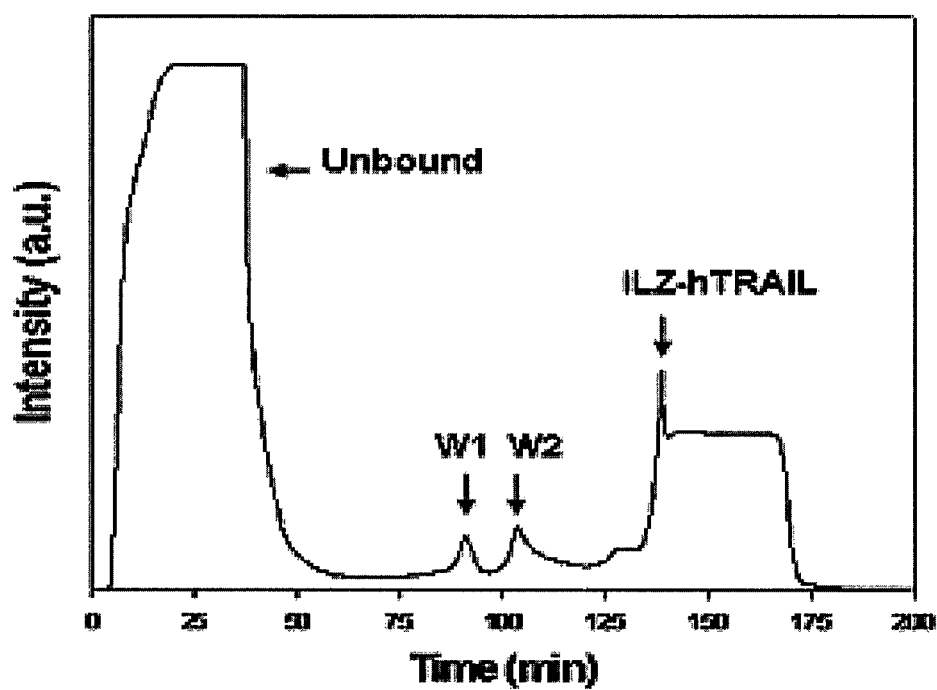
FIG. 2 is a chromatogram of the recombinant hTRAIL purified through Ni-affinity chromatography (washing 1 (w1): washing with 10 mM imidazole-containing phosphate buffer; washing 2 (w2): washing with 50 mM imidazole-containing phosphate buffer)
Figure 3:
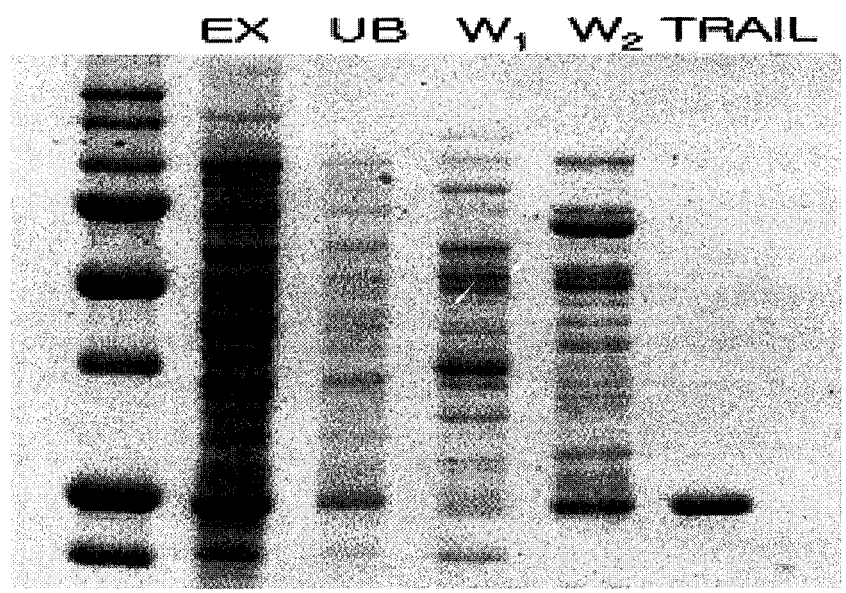
FIG. 3 shows the result of SDS-PAGE of the purified recombinant hTRAIL (EX: *E. coli* lysates; UB: non-pegylated TRAIL; washing 1 (w1): washing with 10 mM imidazole-containing phosphate buffer; washing 2 (w2): washing with 50 mM imidazole-containing phosphate buffer)

FIG. 3 shows the result of SDS-PAGE (14% gel) of the isolated and purified recombinant hTRAIL and elution fractions obtained from the Ni-NTA column (EX: *E. coli* lysates; UB: non-pegylated TRAIL; washing 1 (w1): washing with 10 mM imidazole-containing phosphate buffer; washing 2 (w2): washing with 50 mM imidazole-containing phosphate buffer). As shown in FIG. 2, the recombinant hTRAIL (ILz-hTRAIL) isolated in Example 1-2 was observed to be eluted at a retention time between 135 and 145 min. The electrophoretic result depicted in FIG. 3 indicated that ILz-hTRAIL was successfully isolated and purified using the Ni-NTA column.

1-3: Synthesis and Isolation of PEG-TRAIL Conjugates

The recombinant hTRAIL prepared in Example 1-2 was diluted at 200 µg/ml in 50 mM acetate buffer (pH 5.0), and was mixed with methoxy polyethylene glycol 5000 propionaldehyde (PEG5k). A reducing agent $NaCNBH_3$ was added to the mixture at a final concentration of 20 mM, and the mixture was allowed to react at 4° C. for about 8 to 12 hrs. PEG5k was added to TRAIL at PEG5k reaction molar ratios of 2.5, 5, 7.5 and 10 in order to prepare an N-terminal modified PEG-TRAIL conjugate. Separately, another N-terminal modified PEG-TRAIL conjugate was prepared using methoxy polyethylene glycol 20000 propionaldehyde as described above. The reaction mixtures were subjected to size exclusion chromatography, and the results are given in FIG. 4.

Figure 4:
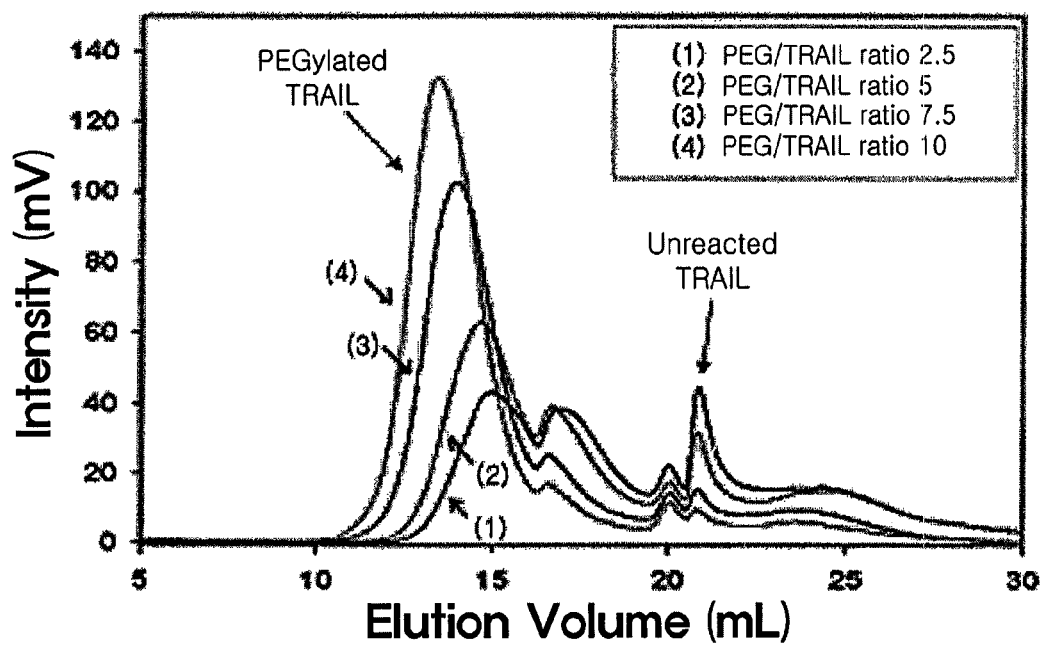
FIG. 4 shows the result of size exclusion chromatography of products according to PEG to TRAIL reaction ratios.

As shown in FIG. 4, the amount of pegylated TRAIL increased with increasing amounts of PEG. However, excessive PEG reacted with side-chain amines of internal lysine residues as well as a desired N-terminal lysine residue, resulting in increased amounts of byproducts. In this case, a resultant conjugate had a higher molecular weight and eluted at an earlier time upon size exclusion chromatography (elution solution: 150 mM NaCl-containing phosphate buffer, pH 6.0). These results indicate that it is effective to set the reaction ratio of PEG to TRAIL within an optimal range so that it is not very high or very low.

An N-terminal modified PEG-TRAIL conjugate, prepared using PEG and TRAIL at a reaction ratio of 7, was isolated and purified through size exclusion chromatography. The results are given in FIG. 5.

Figure 5:
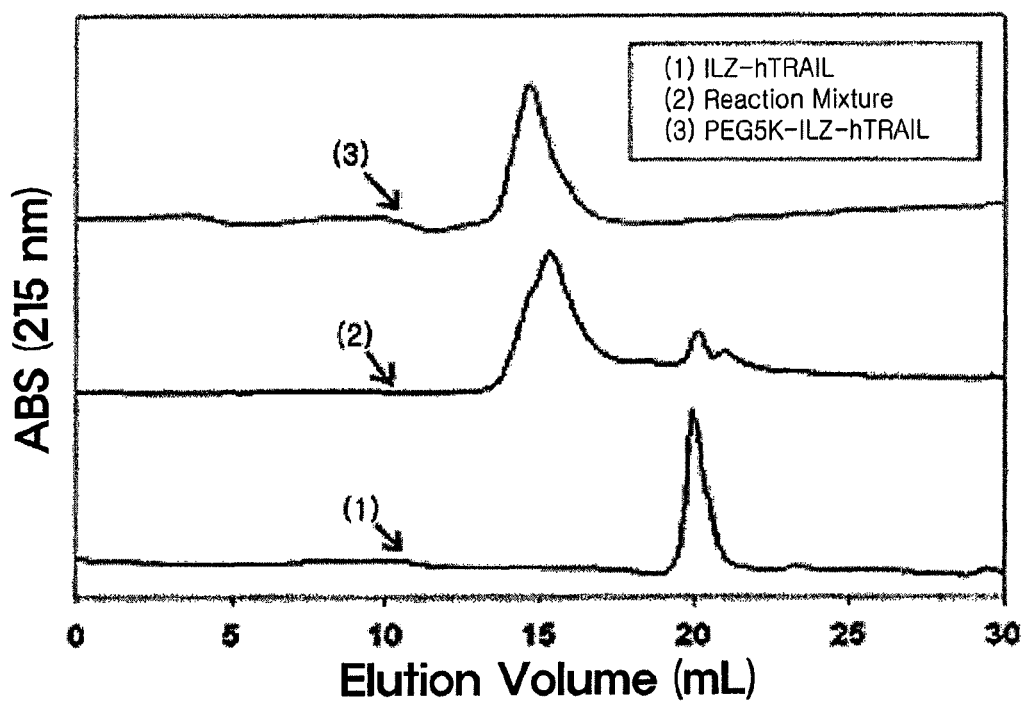
FIG. 5 shows the result of size exclusion chromatography of TRAIL (ILz-hTRAIL), a reaction mixture and a purified N-terminal modified PEG-TRAIL conjugate (PEG5K-ILz-hTRAIL)

As shown in FIG. 5, the purified N-terminal modified PEG-TRAIL conjugate was detected at a relatively higher elution volume compared to the non-pegylated recombinant hTRAIL produced in and isolated from *E. coli*. Also, the chromatogram indicated that the purified N-terminal modified PEG-TRAIL conjugate was highly pure and did not contain any unreacted TRAIL.

Figure 6:
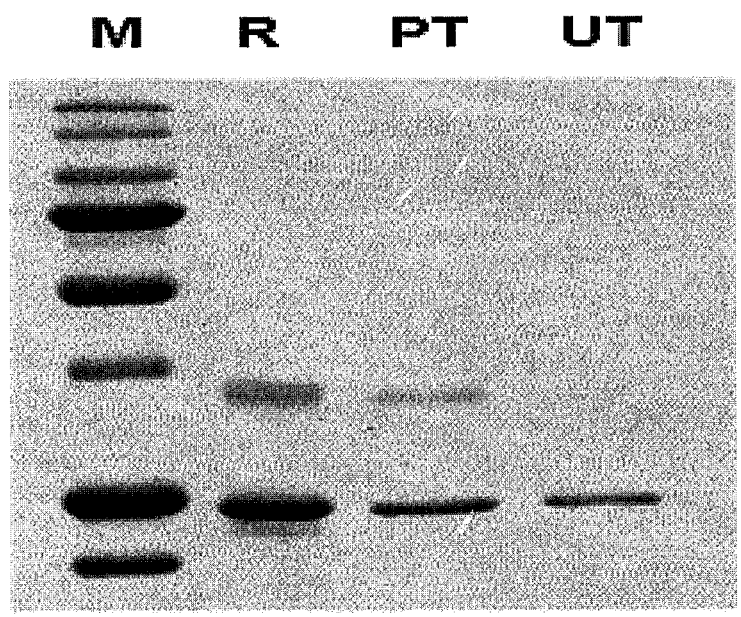
FIG. 6 shows the result of electrophoresis of a reaction mixture, an N-terminal modified PEG-TRAIL conjugate and unreacted TRAIL.

FIG. 6 shows the results of electrophoresis of the reaction mixture of this example, the purified recombinant hTRAIL and the purified N-terminal modified PEG-TRAIL conjugate.

As shown in FIG. 6, when compared to the band of monomeric TRAIL, TRAIL monomers were found to exist in the purified N-terminal modified PEG-TRAIL conjugate. This indicates that PEG was bound to the terminal end of one or two monomers of trimeric TRAIL. Also, on the electrophoresis gel, except for monomeric TRAIL and monomers of the N-terminal modified PEG-TRAIL conjugate, no impurities were observed, indicating that the finally purified pegylated TRAIL had a high purity.

Experimental Example 1

Comparison of Bioactivity of Non-Pegylated TRAIL and N-Terminal Modified PEG-TRAIL Conjugates (Apoptosis Assay)

Non-pegylated TRAIL and the N-terminal modified PEG-TRAIL conjugates were examined for bioactivity, as follows.

An apoptosis assay for the non-pegylated recombinant TRAIL and N-terminal modified PEG-TRAIL conjugates was conducted using human cervical carcinoma HeLa cells and human colon carcinoma HCT116 cells. HeLa cells were cultured in DMEM (Dulbecco's Modified Eagle's Medium), and HCT116 cells in RPMI-1640. Each cell line was seeded onto a 96-well plate at a density of $1 \times 10^4$ cells/well, and was cultured for about 24 hrs to stabilize it. The cells were dosed with control TRAIL (purchased from R&D systems), the recombinant hTRAIL prepared according to the method of Examples 1-1 and 1-2, and the N-terminal modified PEG-TRAIL conjugates (PEG5K-ILz-hTRAIL and PEG20K-ILz-hTRAIL) at a final concentration of 1 ng/ml to 5 µg/ml for about 24 hrs. Then, 20 µl of MTS solution (Promega) was added to each well, and the plate was incubated for about 2 hrs. Absorbance was measured at 490 nm, and cell viability was calculated from the absorbance. The results are given in FIGS. 7, 8 and 9.

Figure 7:
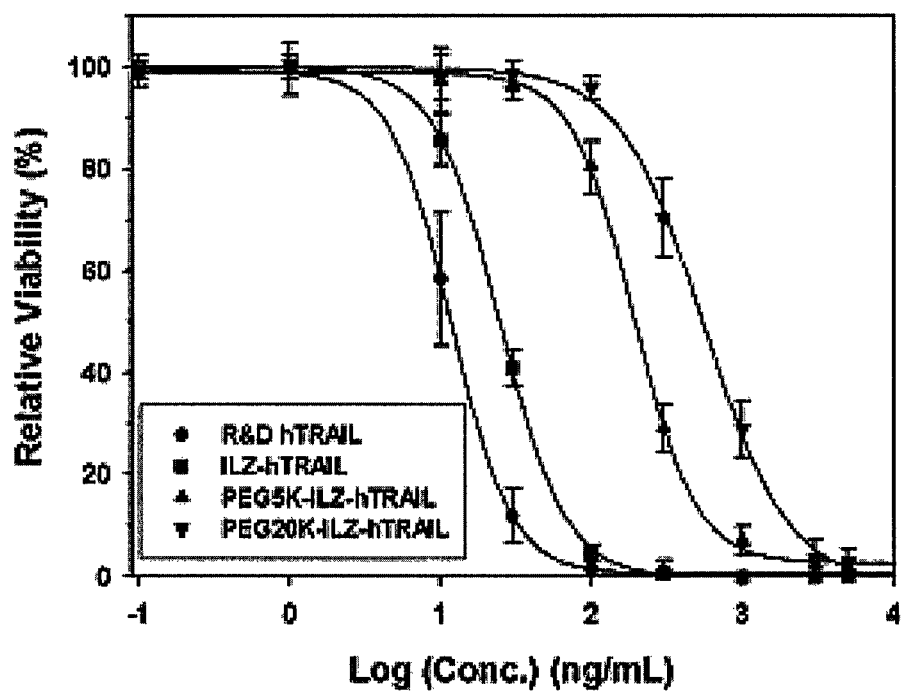
FIG. 7 shows the result of a cytotoxicity assay against human cervical carcinoma HeLa cells according to the molecular weight of PEG.
Figure 8:
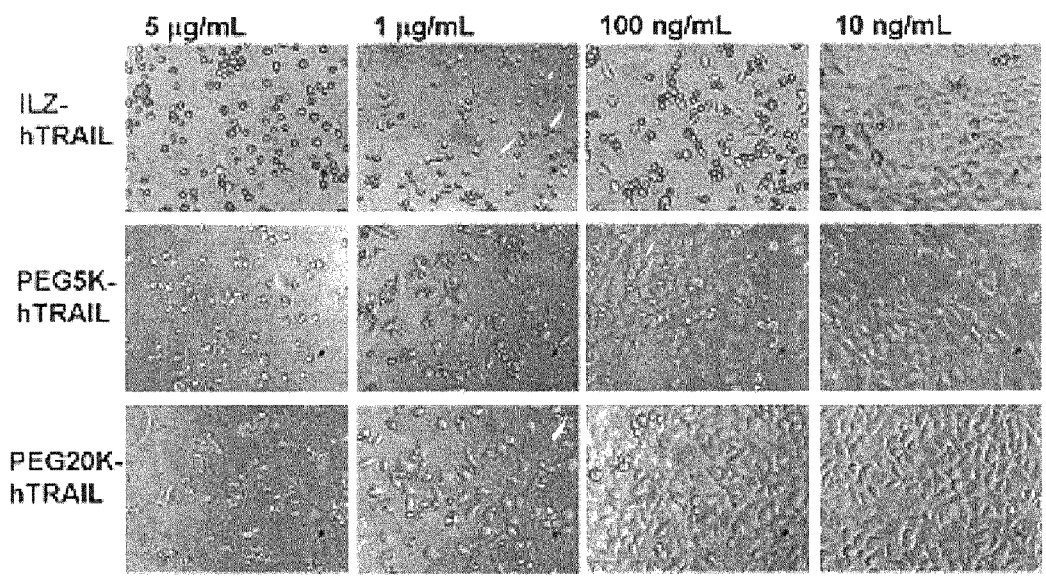
FIG. 8 is a microscopic photograph showing cell viability according to drug concentrations in the cytotoxicity assay against HeLa cells.

As shown in FIGS. 7 and 8, similar to non-pegylated TRAIL, the N-terminal modified PEG-TRAIL conjugates were found to have cytotoxicity against HeLa cells in a dose-dependent manner. The N-terminal modified PEG-TRAIL conjugates were observed to have relatively low cytotoxicity with increasing molecular weight of the attached PEG. These results were consistent with the microscopic results shown in FIG. 8, in which the TRAIL-treated cells were observed microscopically.

Figure 9:
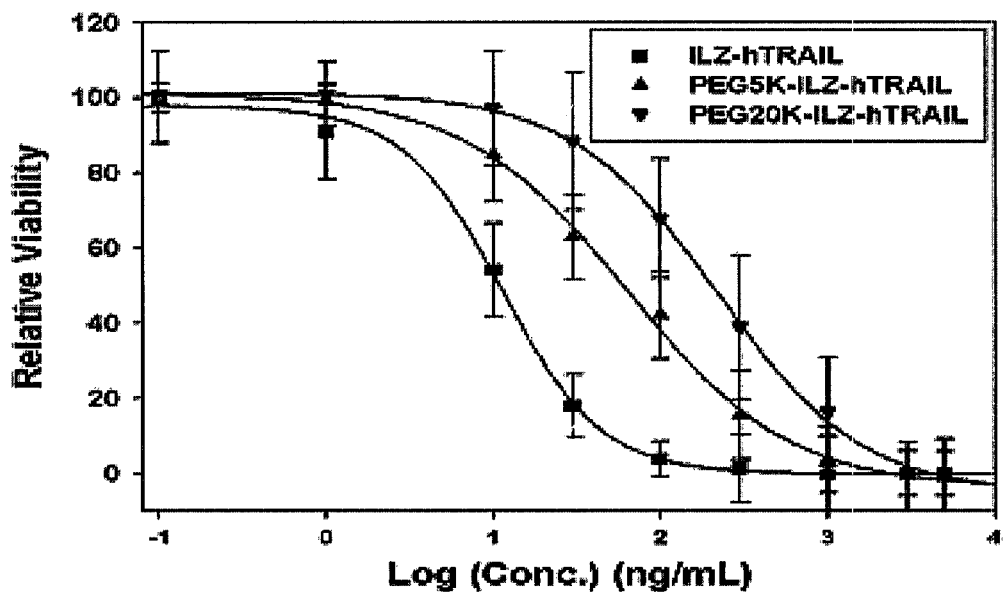
FIG. 9 shows the result of a cytotoxicity assay against human colon carcinoma HCT116 cells according to the molecular weight of PEG.

As shown in FIG. 9, the PEG-TRAIL conjugates exhibited cytotoxicity against colon carcinoma HCT116 cells in a manner similar to that observed in FIG. 7. Also, the PEG effect on cytotoxicity against HCT116 cells was similar to that observed against HeLa cells.

Experimental Example 2

Evaluation of Solution Solubility of N-Terminal Modified PEG-TRAIL Conjugates

The non-pegylated recombinant TRAIL and N-terminal modified PEG-TRAIL conjugates were examined for solution stability, as follows.

The solubility of non-pegylated and pegylated TRAIL was assayed over time in order to investigate the solution stability thereof. The non-pegylated TRAIL and N-terminal modified PEG-TRAIL conjugates were individually prepared at 200 µg/ml in 50 mM acetate buffer, diluted at a 1:1 ratio with 100 mM phosphate buffer to adjust the physiological pH value, and then analyzed for solubility over time at 37° C. Samples were collected in small amounts at 5, 15, 30, 60, 120 and 180 min. The collected samples were centrifuged to separate soluble and precipitated fractions. For the soluble fractions thus obtained (as supernatants), protein concentrations were determined using a BCA protein assay kit. The results are given in FIG. 10.

Figure 10:
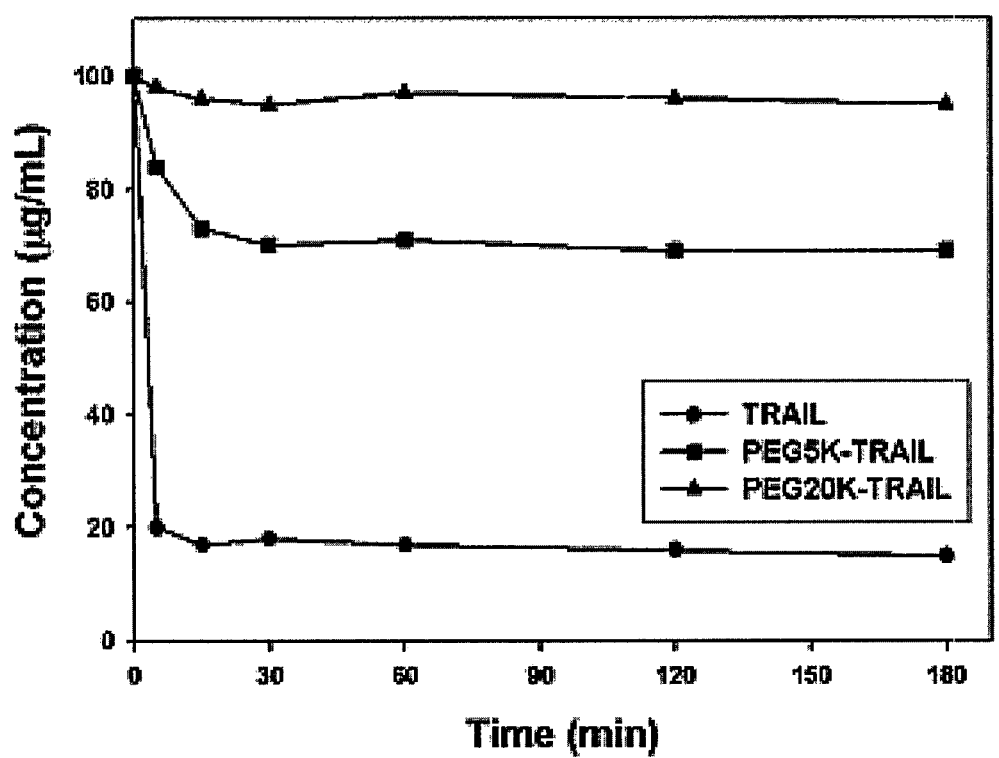
FIG. 10 shows the solution solubility of non-pegylated TRAIL and an N-terminal modified PEG-TRAIL conjugate.

As shown in FIG. 10, a remarkable difference in solution stability was observed between non-pegylated TRAIL and N-terminal modified PEG-TRAIL conjugates. Most non-pegylated TRAIL (more than 80% thereof) was precipitated within 5 min. In contrast, N-terminal modified PEG-TRAIL conjugates exhibited very high solution stability, and this stability increased with increasing molecular weights of PEG. PEG5K-ILz-hTRAIL displayed a stability of about 70%, and PEG20K-ILz-hTRAIL displayed a stability of about 95%.

Experimental Example 3

Evaluation of Pharmacokinetic Profiles of an N-Terminal Modified PEG-TRAIL Conjugate The non-pegylated TRAIL (ILz-hTRAIL) and N-terminal modified PEG-TRAIL conjugate (PEG5K-ILz-hTRAIL) were examined for pharmacokinetic profiles, as follows.

In order to estimate in vivo behavior of the non-pegylated TRAIL and N-terminal modified PEG-TRAIL conjugate, pharmacokinetic analysis was preformed using 6-week-old Sprague-Dawley rats. In order to facilitate the collection of blood samples from the animal; the right jugular vein of each of the rats was cannulated by inserting one end of a length of PE-10 tubing into the jugular vein about 2.5 cm deep, and suturing it in place. The other end of the tubing was passed through the back of the animal and connected to a blood collection tube at the exterior. The rats were then allowed to acclimatize and recover for about 24 hrs. The non-pegylated TRAIL and N-terminal modified PEG-TRAIL conjugate were subcutaneously administered to the rats at a dosage of 10 µg/kg. Blood samples (0.2 ml each) were collected at given time points for a test period of 48 hrs (the first blood sample was collected at 5 min). After the collected blood samples were centrifuged, the plasma samples were analyzed for in vivo behavior of the non-pegylated TRAIL and N-terminal modified PEG-TRAIL conjugate using a human TRAIL ELISA kit. The results are given in FIGS. 11 and 12, respectively.

Figure 11:
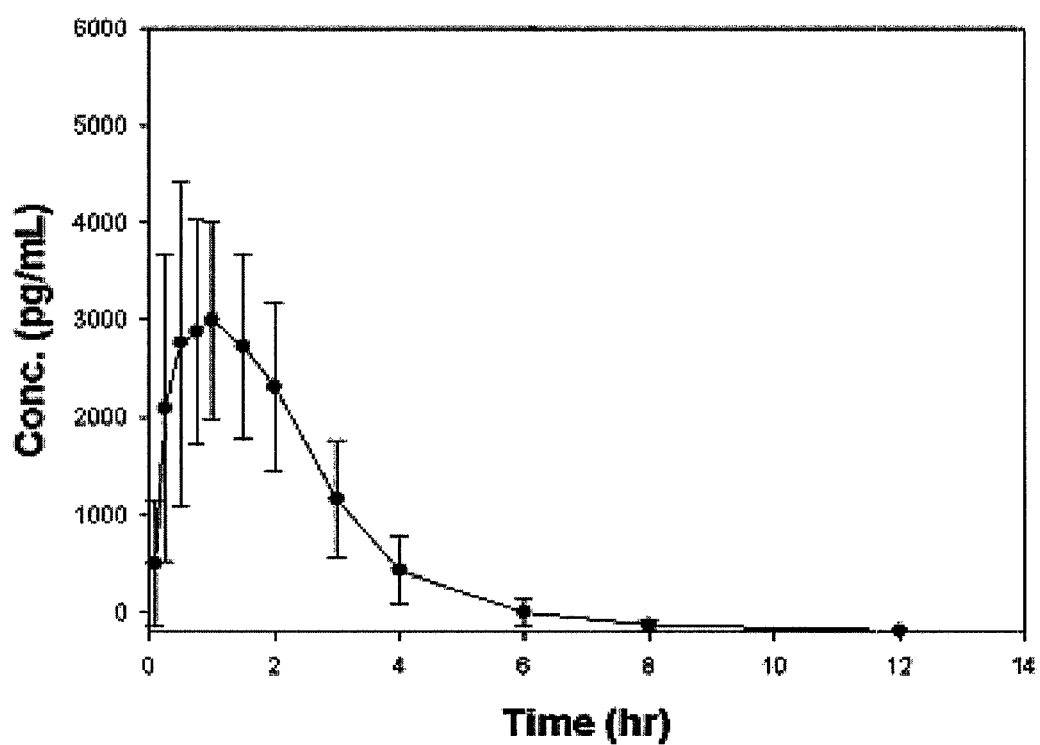
FIG. 11 shows the pharmacokinetic profiles of non-pegylated TRAIL.
Figure 12:
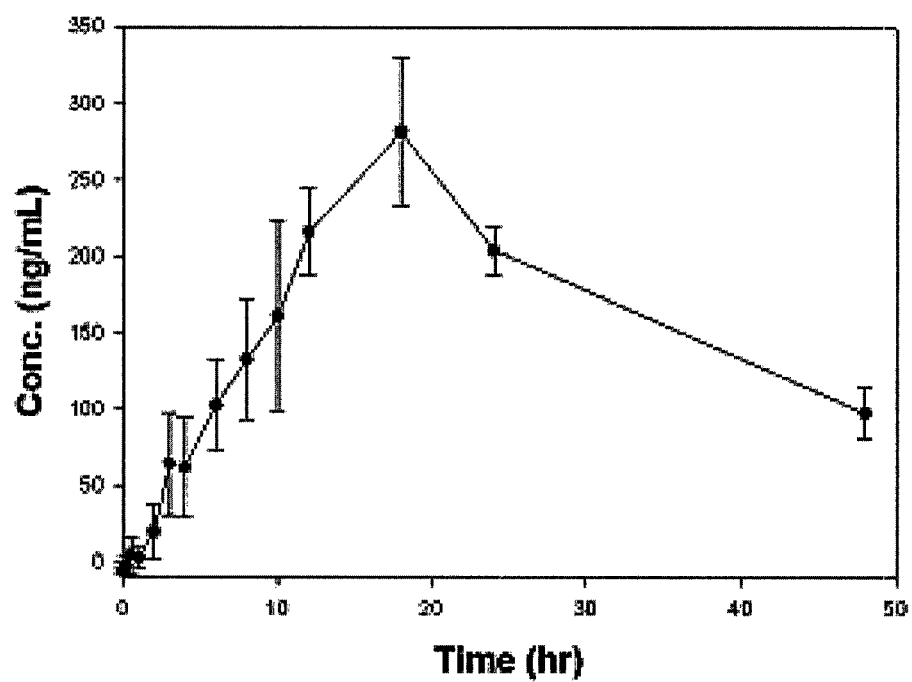
FIG. 12 shows the pharmacokinetic profiles of an N-terminal modified PEG-TRAIL conjugate.

As shown in FIGS. 11 and 12, there was a difference in in vivo behavior between the non-pegylated TRAIL and N-terminal modified PEG-TRAIL conjugate. The non-pegylated TRAIL (ILz-hTRAIL) was rapidly absorbed, and exhibited the highest concentration in the blood after about one hour, but the blood concentration thereof was decreased by rapid renal excretion and metabolization. In contrast, the N-terminal modified PEG-TRAIL conjugate (PEG5K-ILz-hTRAIL) was slowly absorbed from the administered subcutaneous region, and was maintained at high concentrations in the blood for a long period of 48 hrs or longer. This was considered to be due to the low renal excretion and low hepatic metabolization of TRAIL resulting from pegylation.

The results of the pharmacokinetic analysis are given in Table 1.

TABLE 1

Pharmacokinetic profiles of non-pegylated TRAIL and N-terminal modified PEG-TRAIL conjugate

|  | ILz-hTRAIL | PEG5K-ILz-hTRAIL |
| --- | --- | --- |
| AUC (ng · hr/ml) | 7.71 ± 1.1. | 7628.2 ± 321.6 |
| Cmax (ng/ml) | 3.38 ± 0.48 | 298.3 ± 24.8 |
| $T_{max}$ (hr) | 0.96 ± 0.19 | 19.0 ± 1.0 |
| $T_{1/2}$ (hr) | 0.79 ± 0.01 | 24.5 ± 4.0 |

As shown in Table 1, compared to ILz-hTRAIL, PEG5K-ILz-hTRAIL existed at higher levels in blood, and had $T_{max}$ (time to reach maximum concentration) more than 19 times higher and $T_{1/2}$ 30 times longer. These results indicate that the N-terminal modified PEG-TRAIL conjugate according to the present invention is a pharmacokinetically good drug.

Hereinafter, exemplary formulations of the present PEG-TRAIL conjugate will be given.

Formulation Examples

Preparation of Pharmaceutical Formulations

Pharmaceutical formulations comprising the N-terminal modified PEG-TRAIL conjugate according to the present invention were prepared as follows.

1. Preparation of Powders

| N-terminal modified PEG-TRAIL conjugate | 2 g |
| --- | --- |
| Lactose | 1 g |

The above components were mixed and placed in an airtight pack, thereby giving powders.

2. Preparation of Tablets

| | |
|---|---|
| N-terminal modified PEG-TRAIL conjugate | 100 mg |
| Corn starch | 100 mg |
| Lactose | 100 mg |
| Magnesium stearate | 2 mg |

The above components were mixed and tableted according to a common tablet preparation method, thereby giving tablets.

3. Preparation of Capsules

| | |
|---|---|
| N-terminal modified PEG-TRAIL conjugate | 100 mg |
| Corn starch | 100 mg |
| Lactose | 100 mg |
| Magnesium stearate | 2 mg |

The above components were mixed and loaded into gelatin capsules according to a common capsule preparation method, thereby giving capsules.

4. Preparation of Injectable Solution

| | |
|---|---|
| N-terminal modified PEG-TRAIL conjugate | 10 μg/ml |
| Dilute hydrochloric acid BP | up to pH 3.5 |
| Injectable sodium chloride BP | maximum 1 ml |

The N-terminal modified PEG-TRAIL conjugate was dissolved in a suitable volume of injectable sodium chloride BP, and was adjusted to a pH of 3.5 using dilute hydrochloric acid BP. Injectable sodium chloride BP was further added to achieve a desired volume, and the solution was sufficiently mixed. The mixture solution was then filled into a 5-ml type I ampule made of transparent glass. The glass was melted to seal the ampule, which was autoclaved at 120° C. for 15 min, thereby giving an injectable solution.

The invention claimed is:

1. An N-terminal modified PEG (Polyethylene glycol)-TRAIL (tumor necrosis factor-related apoptosis-inducing ligand) conjugate consisting of:
   a trimeric TRAIL comprising SEQ ID NO:2 amino acids 114 to 281 and a zipper amino acid motif present at the N-terminus of each TRAIL monomer; and
   a PEG or a derivative thereof selected from the group consisting of methoxypolyethylene glycol succinimidyl propionate, methoxypolyethylene glycol N-hydroxysuccinimide, methoxypolyethylene glycol aldehyde, methoxypolyethylene glycol maleimide and multiple-branched polyethylene glycol,
   wherein the PEG is bound via a linker having an average molecular weight between one and 30,000 daltons to an amino acid residue in SEQ ID NO:2 amino acids 114 to 281 or the zipper motif in the N-terminal domain of at least one monomer of the trimeric TRAIL, and
   wherein the PEG or the derivative thereof and linker has a molecular weight of between 5,000 and 100,000 daltons as determined by SDS-PAGE.

2. The N-terminal modified PEG-TRAIL conjugate according to claim 1, wherein the PEG or the derivative thereof has a linear or branched form.

3. The N-terminal modified PEG-TRAIL conjugate according to claim 1, wherein the PEG derivative thereof is selected from the group consisting of methoxypolyethylene glycol succinimidyl propionate, methoxypolyethylene glycol N-hydroxysuccinimide, methoxypolyethylene glycol aldehyde, methoxypolyethylene glycol maleimide and multiple-branched polyethylene glycol.

4. The N-terminal modified PEG-TRAIL conjugate according to claim 3, wherein the PEG or the derivative thereof is methoxypolyethylene glycol aldehyde.

5. The N-terminal modified PEG-TRAIL conjugate according to claim 1, wherein the PEG or the derivative thereof and linker has a molecular weight between 5,000 and 40,000 daltons as determined by SDS-PAGE.

6. The N-terminal modified PEG-TRAIL conjugate according to claim 5, wherein the PEG or the derivative thereof and linker has a molecular weight between 10,000 and 40,000 as determined by SDS-PAGE.

7. The N-terminal modified PEG-TRAIL conjugate according to claim 1, wherein each TRAIL monomer in the trimeric TRAIL in the PEG-TRAIL conjugate is human TRAIL, having an amino acid sequence 281 amino acids in length.

8. The N-terminal modified PEG-TRAIL conjugate according to claim 1, wherein each TRAIL monomer in the trimeric TRAIL has an amino acid sequence from arginine-114 to glycine-281 of the human TRAIL.

9. The N-terminal modified PEG-TRAIL conjugate according to claim 8, wherein the zipper amino acid motif is an isoleucine zipper and the PEG is bound to the TRAIL monomer via the N-terminal arginine residue of the monomer of the trimeric TRAIL.

10. The N-terminal modified PEG-TRAIL conjugate according to claim 1, wherein the linker is a polyethylene glycol polymer between 2 and 20,000 daltons in size.

11. A method for preparing the N-terminal modified PEG-TRAIL conjugate of claim 1, comprising reacting an N-terminal amine of one or more monomers of a trimeric TRAIL comprising SEQ ID NO: 2 amino acids 114 to 281 and zipper amino acid motifs at the N-terminals thereof with an aldehyde group of a linker between one and 30,000 daltons or PEG or a derivative thereof selected from the group consisting of methoxypolyethylene glycol succinimidyl propionate, methoxypolyethylene glycol N-hydroxysuccinimide, methoxypolyethylene glycol aldehyde, methoxypolyethylene glycol maleimide and multiple-branched polyethylene glycol, in the presence of a reducing agent, wherein the PEG or derivative thereof and linker attached thereto has an average molecular weight of between 5,000 and 100,000 as determined by SDS-PAGE.

12. The method according to claim 11, wherein the PEG or the derivative thereof has a linear or branched form.

13. The method according to claim 11, wherein the PEG derivative is selected from the group consisting of methoxypolyethylene glycol succinimidyl propionate, methoxypolyethylene glycol N-hydroxysuccinimide, methoxypolyethylene glycol aldehyde, methoxypolyethylene glycol maleimide and multiple-branched polyethylene glycol.

14. The method according to claim 11, wherein the PEG and TRAIL are reacted at a molar ratio (PEG/TRAIL) of 2 to 10.

15. The method according to claim 11, wherein the PEG and TRAIL are reacted at a molar ratio (PEG/TRAIL) of 5 to 7.5.

16. The method according to claim 11, wherein the TRAIL is human TRAIL, having an amino acid sequence 281 amino acids in length.

17. The method according to claim 16, wherein the TRAIL consists of amino acid sequence from arginine-114 to glycine-281 of the full-length human form of SEQ ID NO:2.

18. The method according to claim 11, wherein the zipper amino acid motif is an isoleucine zipper.

19. The method according to claim 11, wherein the reducing agent is $NaCNBH_3$ or $NaBH_4$.

* * * * *

SEQUENCE LISTING

```
<160> NUMBER OF SEQ ID NOS: 2

<210> SEQ ID NO 1
<211> LENGTH: 281
<212> TYPE: PRT
<213> ORGANISM: Homo sapiens

<400> SEQUENCE: 1

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240
```

-continued

```
Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 2
<211> LENGTH: 167
<212> TYPE: PRT
<213> ORGANISM: Homo sapiens

<400> SEQUENCE: 2

Arg Glu Arg Gly Pro Gln Arg Val Ala Ala His Ile Thr Gly Thr Arg
1               5                   10                  15

Gly Arg Ser Asn Thr Leu Ser Ser Pro Asn Ser Lys Asn Glu Lys Ala
            20                  25                  30

Leu Gly Arg Lys Ile Asn Ser Trp Glu Ser Ser Arg Ser Gly His Ser
            35                  40                  45

Phe Leu Ser Asn Leu His Leu Arg Asn Gly Glu Leu Val Ile His Glu
        50                  55                  60

Lys Gly Phe Tyr Tyr Ile Tyr Ser Gln Thr Tyr Phe Arg Phe Gln Glu
65                  70                  75                  80

Glu Ile Lys Glu Asn Thr Lys Asn Asp Lys Gln Met Val Gln Tyr Ile
            85                  90                  95

Tyr Lys Tyr Thr Ser Tyr Pro Asp Pro Ile Leu Leu Met Lys Ser Ala
            100                 105                 110

Arg Asn Ser Cys Trp Ser Lys Asp Ala Glu Tyr Gly Leu Tyr Ser Ile
            115                 120                 125

Tyr Gln Gly Gly Ile Phe Glu Leu Lys Glu Asn Asp Arg Ile Phe Val
        130                 135                 140

Ser Val Thr Asn Glu His Leu Ile Asp Met Asp His Glu Ala Ser Phe
145                 150                 155                 160

Phe Gly Ala Phe Leu Val Gly
            165
```